(12) United States Patent
Kwon et al.

(10) Patent No.: US 11,434,209 B2
(45) Date of Patent: Sep. 6, 2022

(54) METHOD FOR SYNTHESIS OF TKX-50 USING INSENSITIVE INTERMEDIATE

(71) Applicant: AGENCY FOR DEFENSE DEVELOPMENT, Daejeon (KR)

(72) Inventors: Kuk Tae Kwon, Daejeon (KR); Woong Hee Lee, Daejeon (KR); Jeong Sub Shim, Daejeon (KR); So Jung Lee, Daejeon (KR)

(73) Assignee: AGENCY FOR DEFENSE DEVELOPMENT, Daejeon (KR)

( * ) Notice: Subject to any disclaimer, the term of this patent is extended or adjusted under 35 U.S.C. 154(b) by 0 days.

(21) Appl. No.: 16/969,177

(22) PCT Filed: Aug. 5, 2019

(86) PCT No.: PCT/KR2019/009723
§ 371 (c)(1),
(2) Date: Jan. 25, 2021

(87) PCT Pub. No.: WO2020/040448
PCT Pub. Date: Feb. 27, 2020

(65) Prior Publication Data
US 2021/0163428 A1    Jun. 3, 2021

(30) Foreign Application Priority Data
Aug. 21, 2018  (KR) .......................... 10-2018-0097396

(51) Int. Cl.
*C07D 257/04* (2006.01)
*C06B 25/34* (2006.01)

(52) U.S. Cl.
CPC ............ *C07D 257/04* (2013.01); *C06B 25/34* (2013.01)

(58) Field of Classification Search
CPC ..................................................... C07D 257/04
See application file for complete search history.

(56) References Cited

FOREIGN PATENT DOCUMENTS

| CN | 103524444 | 1/2014 |
| CN | 104829548 | 8/2015 |

OTHER PUBLICATIONS

Fischer et al., "Pushing the limits of energetic materials—the synthesis and characterization of dihydroxylammonium 5,5'-bistetrazole-1,1'-diolate," Journal of Materials Chemistry, 2012, vol. 22, pp. 20418-20422.
Lee et al., "Safe Synthesis of TKX-50 using an Insensitive Intermediate," Propellants, Explosives, Pyrotechnics, 2019, vol. 44, 5 pages.
Sabatini et al., "Recent Advances in the Synthesis of High Explosive Materials," Crystals, 2016, vol. 6, No. 5, 22 pages.
WIPO, ISR for PCT/KR2019/009723, Oct. 29, 2019.

*Primary Examiner* — Shawquia Jackson
(74) *Attorney, Agent, or Firm* — Hodgson Russ LLP

(57) ABSTRACT

The present disclosure relates to a method for synthesis of TKX-50 using an insensitive intermediate, and more specifically, to a method of manufacturing TKX-50 which includes: preparing DCG as a starting material; forming a THP-DAG intermediate from the DCG; and synthesizing TKX-50 through the THP-DAG intermediate.

15 Claims, 8 Drawing Sheets

METHOD FOR SYNTHESIS OF TKX-50 USING INSENSITIVE INTERMEDIATE

CROSS-REFERENCE TO RELATED APPLICATIONS

This application is a U.S. national phase application of International Application No. PCT/KR2019/009723, filed on Aug. 5, 2019, which claims priority to Korean Patent Application No. 10-2018-0097396, filed on Aug. 21, 2018. The entire disclosures of the aforementioned applications are incorporated herein by reference.

TECHNICAL FIELD

The present invention relates to a method for synthesizing TKX-50 using an insensitive intermediate.

BACKGROUND ART

Currently, the most widely used high-energy materials for military explosive are 1,3,5-trinitro-1,3,5-triazacyclohexane (RDX), 1,3,5,7-tetranitro-1,3,5,7-tetraazacyclooctane (HMX), 2,4,6,8,10,12-hexanitro-2,4,6,8,10,12-hexazaisowurtzitane (CL-20), and the like, and are being used in a wide variety of fields. Recently, with the development of new weapon systems, many studies are being conducted to develop high-energy materials with higher explosive performance than high-energy materials that are previously used. In particular, research on materials containing ring or cage structures has been actively conducted. Among the developed high-energy materials, dinitroazofuroxane (DDF) and octanitrocubane (ONC) have a very excellent explosive performance with a detonation velocity of about 10,000 m/s, but are very sensitive, and thus have a critical drawback of threatening safety of a person handling the DDF and ONC.

Recently, to enhance an explosive performance and an insensitivity, research is being actively conducted on cyclic compounds with a high nitrogen content such as triazole, tetrazole, nitroiminotetrazole, tetrazine, and the like. Among such cyclic compounds, dihydroxylammonium 5,5'-bistetrazole-1,1'-diolate (TKX-50) that is a tetrazole compound is regarded as one of promising high-energy materials. TKX-50 is known to have a higher explosive performance than those of existing energy materials (RDX, HMX, CL-20), and also to be insensitive.

FIG. 1 illustrates an existing synthesis method of TKX-50. Referring to FIG. 1, the existing synthesis method of TKX-50 is performed through five synthesis steps using glyoxal as a starting material. TKX-50 itself is insensitive in comparison to existing high-energy materials, but diazidoglyoxime (DAG), which is an intermediate obtained after an azidation reaction that introduces an energy group, has a very high sensitivity (DAG: impact sensitivity of 1.5 J, friction sensitivity of 5 N or less, and electrostatic sensitivity of 7 mJ) at a level of a primary explosive (lead styphnate: impact sensitivity of 2.5 to 5 J and friction sensitivity of 1.5 N, and lead azide: impact sensitivity of 2.5 to 4 J and friction sensitivity of 0.1 to 1 N). Accordingly, the DAG threatens safety of an operator during a synthesis of TKX-50 and also has a danger of an accident.

DISCLOSURE OF THE INVENTION

Technical Subject

One or more example embodiments of the present invention are to solve the above-mentioned problems, and an aspect of the present invention is to provide a method for synthesizing TKX-50 through relatively insensitive O,O'-ditetrahydropyranyloxalohydroximoyl diazide (THP-DAG), instead of using DAG that is a sensitive intermediate, so that an operator may more safely work when synthesizing TKX-50.

However, the problems to be solved by the present invention are not limited to the aforementioned problems, and other problems to be solved, which are not mentioned above, will be clearly understood by a person having ordinary skill in the art from the following description.

Technical Solution

According to an example embodiment of the present invention, there is provided a method for manufacturing TKX-50, the method including: preparing DCG as a starting material; forming a THP-DAG intermediate from the DCG; and synthesizing TKX-50 through the THP-DAG intermediate.

According to an aspect, the TKX-50 may be free of diazidoglyoxime (DAG) that is an intermediate byproduct.

According to an aspect, the THP-DAG may have a impact sensitivity of 15 J or greater, a friction sensitivity of 300 N or greater and an electrostatic sensitivity of 40 mJ or greater.

According to an aspect, the method may include synthesizing dichloroglyoxime (DCG); synthesizing THP-DCG through the DCG; synthesizing THP-DAG through the THP-DCG; and synthesizing TKX-50 through the THP-DAG.

According to an aspect, the synthesizing of the dichloroglyoxime (DCG) may include synthesizing glyoxime; and reacting the glyoxime with N-chlorosuccinimide.

According to an aspect, the synthesizing of the THP-DCG through the DCG may be performed by reacting the DCG with 3,4-dihydro-2H-pyran in the presence of a p-toluenesulfonic acid (p-TsOH) catalyst.

According to an aspect, the synthesizing of the THP-DCG through the DCG may be performed by stirring and reacting the DCG, the p-TsOH and the 3,4-dihydro-2H-pyran at a weight ratio of 1:3 to 4:1.6.

According to an aspect, stirring of the DCG, the p-TsOH and the 3,4-dihydro-2H-pyran may be performed at room temperature.

According to an aspect, the synthesizing of the THP-DAG through the THP-DCG may be performed through an azidation reaction.

According to an aspect, the synthesizing of the THP-DAG through the THP-DCG may be performed by reacting the THP-DCG with sodium azide ($NaN_3$).

According to an aspect, the THP-DCG and the sodium azide may be stirred at a weight ratio of 1:0.4 to 0.8 and reacted.

According to an aspect, stirring of the THP-DCG and the sodium azide may be performed at a temperature of 95° C. to 100° C.

According to an aspect, the synthesizing of the TKX-50 through the THP-DAG may include synthesizing 5,5'-bistetrazole-1,1'-diol by reacting the THP-DAG with a hydrochloric acid gas; and synthesizing the TKX-50 by reacting the 5,5'-bistetrazole-1,1'-diol with hydroxylamine.

According to an aspect, the synthesizing of the 5,5'-bistetrazole-1,1'-diol by reacting the THP-DAG with the hydrochloric acid gas may be performed by stirring the THP-DAG and the hydrochloric acid under a temperature condition of room temperature.

According to an aspect, the synthesizing of the TKX-50 by reacting the 5,5'-bistetrazole-1,1'-diol with the hydroxylamine may be performed by stirring and reacting the 5,5'-bistetrazole-1,1'-diol and the hydroxylamine at a weight ratio of 1:0.5 to 0.7.

According to an aspect, stirring of the 5,5'-bistetrazole-1,1'-diol and the hydroxylamine may be performed at a temperature of 40° C. to 60° C.

Effect of the Invention

According to the present invention, a relatively insensitive THP-DAG intermediate may be used instead of DAG that is a sensitive intermediate during a synthesis of TKX-50, and thus an operator may more safely work when synthesizing TKX-50.

BEST MODE FOR CARRYING OUT THE INVENTION

Figure 1:
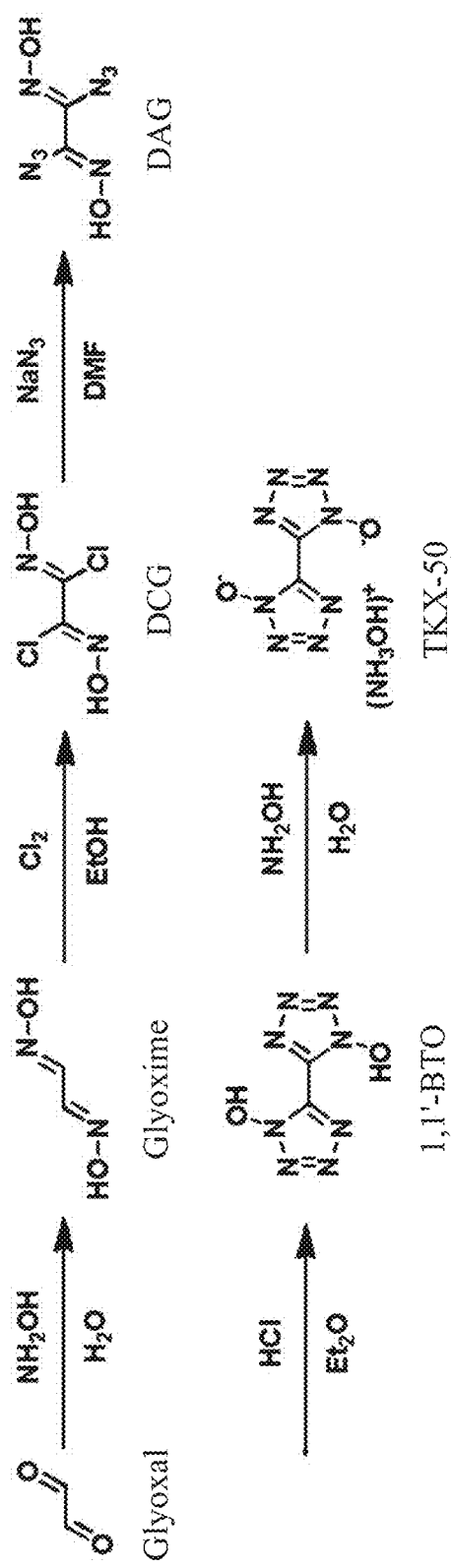
FIG. 1 illustrates an existing synthesis method of TKX-50.

Hereinafter, example embodiments of the present invention will be described in detail with reference to the accompanying drawings. When it is determined detailed description related to a related known function or configuration they may make the purpose of the present invention unnecessarily ambiguous in describing the present invention, the detailed description will be omitted here. Also, terminologies used herein are defined to appropriately describe the example embodiments and thus may be changed depending on a user, the intent of an operator, or a custom of a field to which the present invention pertains. Accordingly, the terminologies must be defined based on the following overall description of the present specification. The same reference numerals as shown in each drawing represent same elements.

Throughout the specification, when any element is positioned "on" the other element, this not only includes a case that the any element is brought into contact with the other element, but also includes a case that another element exists between two elements.

Throughout the specification, if a prescribed part "includes" a prescribed element, this means that another element can be further included instead of excluding other elements unless any particularly opposite description exists.

Hereinafter, a method for manufacturing TKX-50 will be described in detail with reference to example embodiments and drawings. However, the present invention is not limited to the example embodiments and drawings.

Figure 2:
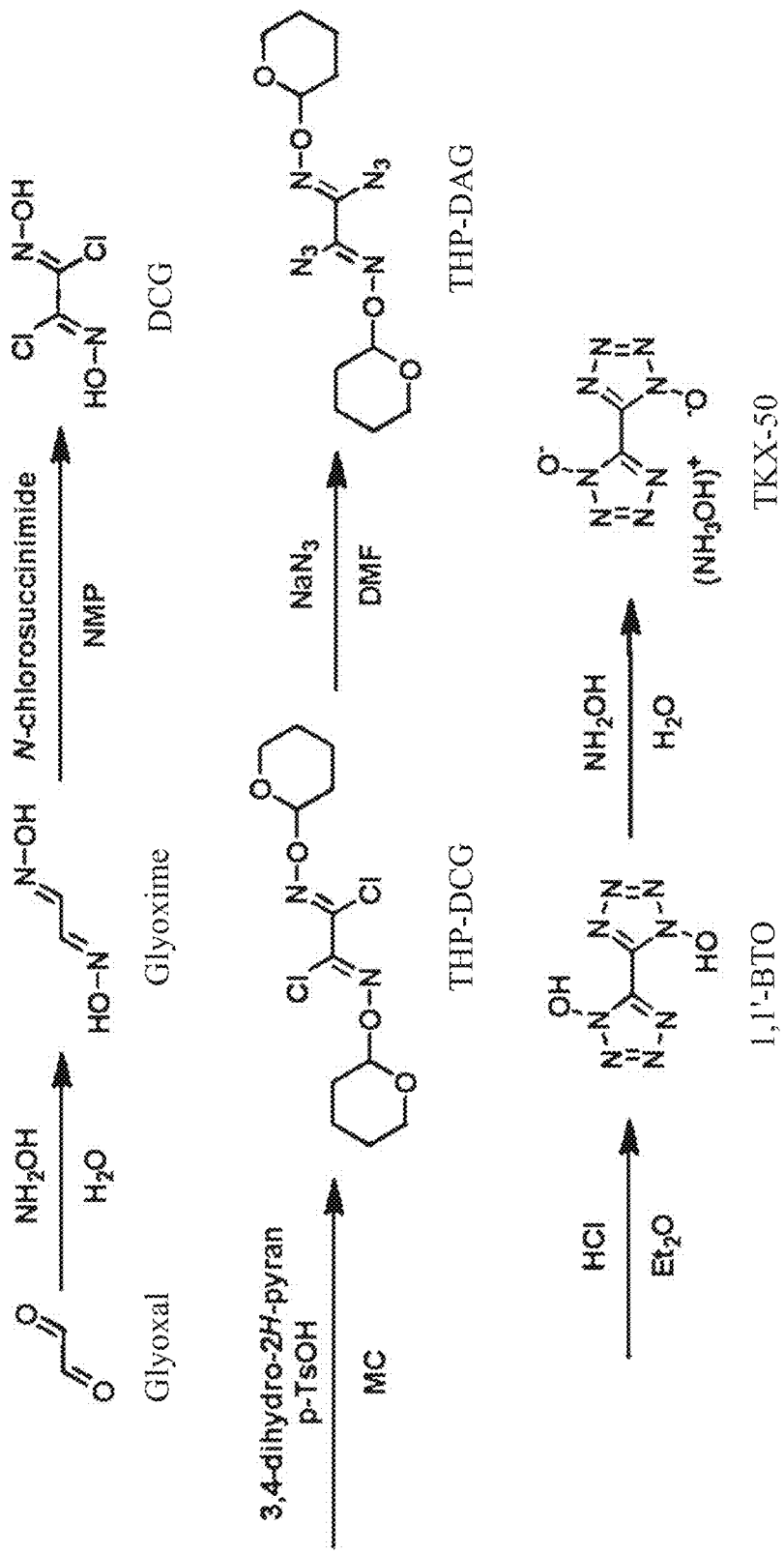
FIG. 2 illustrates a method for manufacturing TKX-50 according to an example embodiment of the present invention.

FIG. 2 illustrates a method for manufacturing TKX-50 according to an example embodiment of the present invention. Hereinafter, the present invention is described with reference to FIG. 2.

The method for manufacturing TKX-50 according to an example embodiment of the present invention includes preparing dichloroglyoxime (hereinafter, referred to as "DCG") as a starting material; forming O,O'-ditetrahydropyranyl oxalohydroximoyl diazide (hereinafter, referred to as "THP-DAG") intermediate from the DCG; and synthesizing dihydroxylammonium 5,5'-bistetrazole-1,1'-diolate (hereinafter, referred to as "TKX-50") through the THP-DAG intermediate.

According to an aspect, the TKX-50 may be free of diazidoglyoxime (hereinafter, referred to as "DAG") that is an intermediate byproduct.

In other words, a relatively insensitive THP-DAG intermediate may be used instead of DAG that is a sensitive intermediate, when TKX-50 is synthesized, and thus an operator may more safely synthesize the TKX-50.

According to an aspect, the THP-DAG may have a impact sensitivity of 15 J or greater, a friction sensitivity of 300 N or greater and an electrostatic sensitivity of 40 mJ or greater.

Table 1 shows sensitivity characteristics of DAG and THP-DAG. More specifically, results obtained by measuring a impact sensitivity, a friction sensitivity and an electrostatic sensitivity of the THP-DAG using a BAM Fall Hammer, a BAM Friction Tester and an Electrostatic Spark Sensitivity Tester are shown.

TABLE 1

|  | Impact sensitivity [J] | Friction sensitivity [N] | Electrostatic sensitivity [mJ] |
| --- | --- | --- | --- |
| DAG | 1.5 | <5 | 7 |
| THP-DAG | 19.95 | 352.8 | 50 |

Referring to Table 1, it is confirmed that the THP-DAG having a impact sensitivity of 19.95 J, a friction sensitivity of 352.8 N and an electrostatic sensitivity of 50 mJ is more insensitive than the DAG. In particular, referring to the impact sensitivity/friction sensitivity of the THP-DAG, the THP-DAG is much less sensitive than a high-energy material that is already in use. It is possible to perform work more safely than using existing synthesis methods from threats of explosion and fire accidents caused by shock/friction/static electricity in handling of the THP-DAG.

According to an aspect, the method may include synthesizing dichloroglyoxime (DCG); synthesizing O,O'-ditetrahydropyranyl oxalohydroximoyl dichloride (hereinafter, referred to as "THP-DCG") through the DCG; synthesizing THP-DAG through the THP-DCG; and synthesizing TKX-50 through the THP-DAG.

According to an aspect, the synthesizing of the dichloroglyoxime (DCG) may include synthesizing glyoxime; and reacting the glyoxime with N-chlorosuccinimide.

According to an aspect, the synthesizing of the THP-DCG through the DCG may be performed by reacting the DCG with 3,4-dihydro-2H-pyran in the presence of a p-toluenesulfonic acid (p-TsOH) catalyst.

According to an aspect, the synthesizing of the THP-DCG through the DCG may be performed by stirring and reacting the DCG, the p-TsOH and the 3,4-dihydro-2H-pyran at a weight ratio of 1:3 to 4:1.6. Desirably, the stirring and reacting of the DCG, the p-TsOH and the 3,4-dihydro-2H-pyran may be performed at a weight ratio of 1:3.7:1.6.

When the weight ratio is outside the above-described weight ratio, a yield may be reduced or impurities may increase.

According to an aspect, stirring of the DCG, the p-TsOH and the 3,4-dihydro-2H-pyran may be performed at room temperature. When the stirring is performed under a temperature condition outside the room temperature, a side reaction may occur.

As an example, the synthesizing of the THP-DCG through the DCG may include adding 10 g (63.7 mmol) of DCG, 300 mL of MC, 36.7 g (191.4 mmol) of p-TsOH, and 16.1 g (191.4 mmol) of 3,4-dihydro-2H-pyran to a reactor, followed by stirring at room temperature for 2 hours, 2) adding 300 mL of distilled water, transferring a reaction solution to a separatory funnel and performing extraction with 200 mL of MC and 200 mL of distilled water three times, and 3) evaporating the MC under reduced pressure and performing purification by a column chromatography to obtain THP-DCG.

According to an aspect, the synthesizing of the THP-DAG through the THP-DCG may be performed through an azidation reaction.

According to an aspect, the synthesizing of the THP-DAG through the THP-DCG may be performed by reacting the THP-DCG with sodium azide ($NaN_3$).

According to an aspect, the THP-DCG and the sodium azide may be stirred at a weight ratio of 1:0.4 to 0.8 and reacted. Desirably, the THP-DCG and the sodium azide may be stirred at a weight ratio of 1:0.6 and reacted.

When the weight ratio is outside the above-described weight ratio, a yield may be reduced or impurities may increase.

According to an aspect, stirring of the THP-DCG and the sodium azide may be performed at a temperature of 95° C. to 100° C. When the stirring is performed under a temperature condition outside the temperature of 95° C. to 100° C., the reaction may be less performed, which may result in a decrease in a yield or a side reaction.

As an example, the synthesizing of the THP-DAG through the THP-DCG may include 1) adding 5 g (15.4 mmol) of THP-DCG, 100 mL of DMF and 3.0 g (46.2 mmol) of NaN3, raising an internal temperature of a reactor to 100° C. and performing stirring for 2 hours, followed by cooling to room temperature, and 2) adding 100 mL of distilled water, precipitating the THP-DAG and performing filtration to obtain the THP-DAG.

According to an aspect, the synthesizing of the TKX-50 through the THP-DAG may include synthesizing 5,5'-bistetrazole-1,1'-diol by reacting the THP-DAG with a hydrochloric acid gas; and synthesizing the TKX-50 by reacting the 5,5'-bistetrazole-1,1'-diol with hydroxylamine.

According to an aspect, the synthesizing of the 5,5'-bistetrazole-1,1'-diol by reacting the THP-DAG with the hydrochloric acid gas may be performed by stirring the THP-DAG and the hydrochloric acid under a temperature condition of room temperature.

As an example, the synthesizing of the 5,5'-bistetrazole-1,1'-diol by reacting the THP-DAG with the hydrochloric acid gas, 1) adding 1.5 g (4.43 mmol) of THP-DAG and 50 mL of diethyl ether to the reactor, followed by cooling to 0° C. and injecting an HCl gas into the reactor for 1 hour, 2) sealing the reactor, raising the internal temperature of the reactor to room temperature and performing stirring for 24 hours, and 3) performing filtration and drying to obtain 1,1'-BTO.

According to an aspect, the synthesizing of the TKX-50 by reacting the 5,5'-bistetrazole-1,1'-diol with the hydroxylamine may be performed by stirring and reacting the 5,5'-bistetrazole-1,1'-diol and the hydroxylamine at a weight ratio of 1:0.5 to 0.7. Desirably, the stirring and reacting of the 5,5'-bistetrazole-1,1'-diol and the hydroxylamine may be performed at a weight ratio of 1:0.64.

When the weight ratio is outside the above-described weight ratio, a yield may be reduced or impurities may increase.

According to an aspect, stirring of the 5,5'-bistetrazole-1,1'-diol and the hydroxylamine may be performed at a temperature of 40° C. to 60° C. Desirably, the stirring may be performed at 50° C. When the stirring is performed under a temperature condition outside the temperature of 40° C. to 60° C., a reaction yield may decrease, or impurities may increase.

As an example, the synthesizing of the TKX-50 by reacting the 5,5'-bistetrazole-1,1'-diol with the hydroxylamine may include 1) adding 1 g (4.85 mmol) of 1,1'-BTO and 20 mL of distilled water to the reactor, raising the internal temperature of the reactor to 50° C. and adding 0.64 g (9.7 mmol) of NH2OH (50% w/w in H2O), and 2) performing stirring at 50° C. for 30 minutes, followed by cooling to room temperature such that TKX-50 is precipitated, and then performing filtration and drying to obtain the TKX-50.

Hereinafter, the present invention will be described in more detail with reference to examples and comparative examples.

However, the following example is given to illustrate the present invention, and the present invention is not limited to the examples.

Example 1: Synthesis of Glyoxime 18.4 g (0.46 mol) of NaOH and 50 mL of distilled water were added to a reactor, cooled to 0° C., and 46 g (0.66 mol) of hydroxylammonium chloride was added to the reactor. Subsequently, 47.9 g (0.33 mol) of 40% glyoxal aqueous solution was added to the reactor while maintaining a temperature of 0 to 10° C. When a solid is produced after stirring for 1 hour while maintaining an internal temperature of the reactor at 0° C., filtration, and washing with a small amount of ice water were performed. Subsequently, drying was performed to obtain 24.7 g (0.28 mol, 85%) of glyoxime.

Example 2: Synthesis of DCG Through Glyoxime 18 g (0.20 mol) of glyoxime and 180 mL of DMF were added to the reactor, cooled to 0° C., and 54.5 g (0.40 mol) of N-chlorosuccinimide was slowly added to the reactor. Subsequently, stirring was performed for 30 minutes while maintaining the internal temperature of the reactor at 0° C., the internal temperature was slowly raised to 25° C., and stirring was performed for 1 hour. Subsequently, after 200 mL of distilled water was added, a reaction solution was transferred to a separatory funnel and extraction was performed with 200 mL of EA and 150 mL of distilled water three times. After evaporating the obtained organic layer under reduced pressure, crude DCG was obtained. The obtained crude DCG and 100 mL of MC were added to the reactor and stirred at room temperature for 1 hour, followed by filtration. Subsequently, drying was performed to obtain 25.4 g (0.16 mol, 81%) of DCG.

Example 3: Synthesis of THP-DCG Through DCG 10 g (63.7 mmol) of DCG, 300 mL of MC, 36.7 g (191.4 mmol) of p-TsOH and 16.1 g (191.4 mmol) of 3,4-dihydro- 2H-pyran were added to the reactor and stirred at room temperature for 2 hours. Subsequently, after 300 mL of distilled water was added, a reaction solution was transferred to a separatory funnel and extraction was performed with 200 mL of MC and distilled water of 200 mL three times. Subsequently, MC was evaporated under reduced pressure and purified by a column chromatography to obtain 14.9 g (45.9 mmol, 72%) of THP-DCG.

Example 4: Synthesis of THP-DAG Through THP-DCG 5 g (15.4 mmol) of THP-DCG, 100 mL of DMF, and 3.0 g (46.2 mmol) of NaN3 were added to the reactor. The internal temperature of the reactor was raised to 100° C. and stirring was performed for 2 hours, followed by cooling to room temperature. Subsequently, 100 mL of distilled water was added to precipitate THP-DAG, followed by filtration, to obtain 2.81 g (8.32 mmol, 54%) of THP-DAG.

Example 5: Synthesis of 1,1'-BTO Through THP-DAG 1.5 g (4.43 mmol) of THP-DAG and 50 mL of diethyl ether were added to the reactor and cooled to 0° C., and an HCl gas was injected into the reactor for 1 hour. Subsequently, the reactor was sealed and raised to room temperature and stirring was performed for 24 hours. When 1,1'-BTO is precipitated, filtration and drying were performed, to obtain 0.6 g (2.75 mmol, 62%) of 1,1'-BTO.

Example 6: Synthesis of TKX-50 Through 1,1'-BTO 1 g (4.85 mmol) of 1,1'-BTO and 20 mL of distilled water were added to the reactor, the internal temperature of the reactor was raised to 50° C., and 0.64 g (9.7 mmol) of NH2OH (50% w/w in H2O) was added. After stirring at 50° C. for 30 minutes, followed by cooling to room temperature, TKX-50 was precipitated. Subsequently, filtration and drying were performed to obtain 0.45 g (2.23 mmol, 46%) of TKX-50.

Figure 3A:
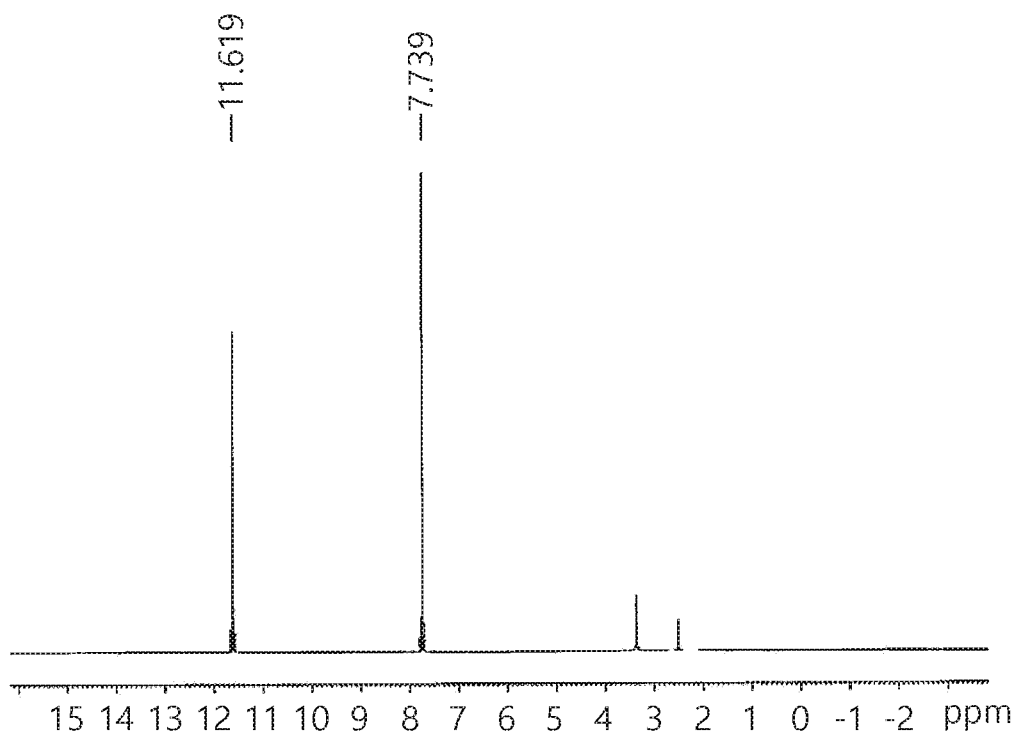
FIG. 3 illustrates NMR graphs of glyoxime synthesized in Example 1 of the present invention.
Figure 3B:
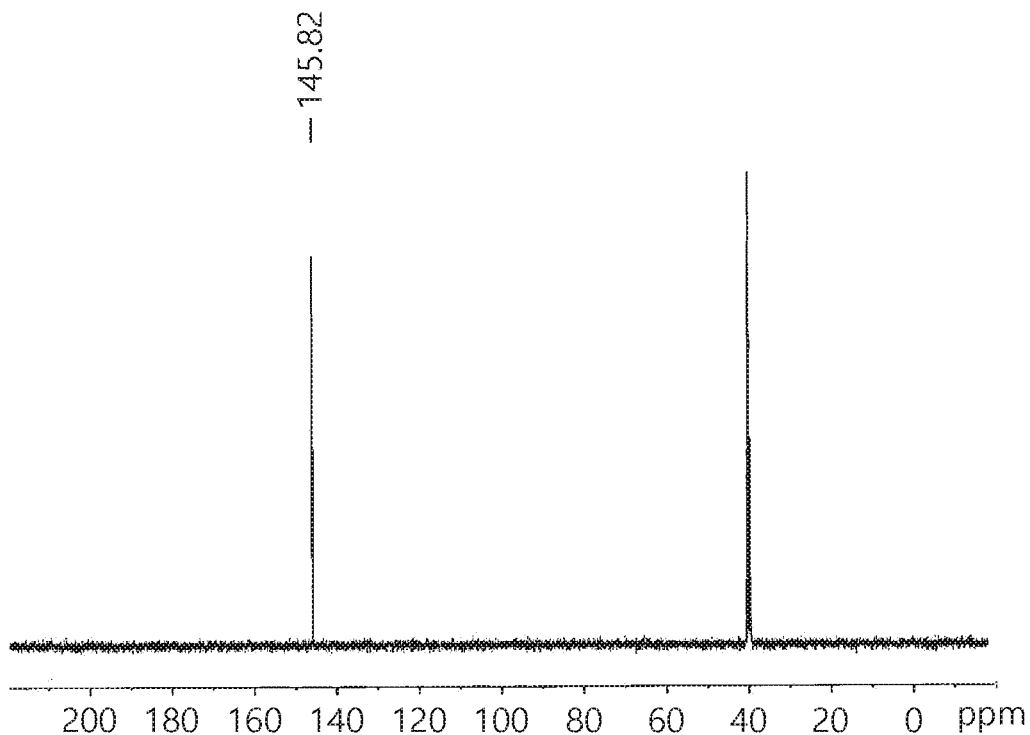

FIG. 3 illustrates NMR graphs of the glyoxime synthesized in Example 1 of the present invention. More specifically, FIG. 3A is a $^1$H NMR spectrum of the glyoxime and FIG. 3B is a $^{13}$C NMR spectrum of the glyoxime.

Referring to FIGS. 3A and 3B, it may be found that the glyoxime was synthesized based on Example 1.

Figure 4A:
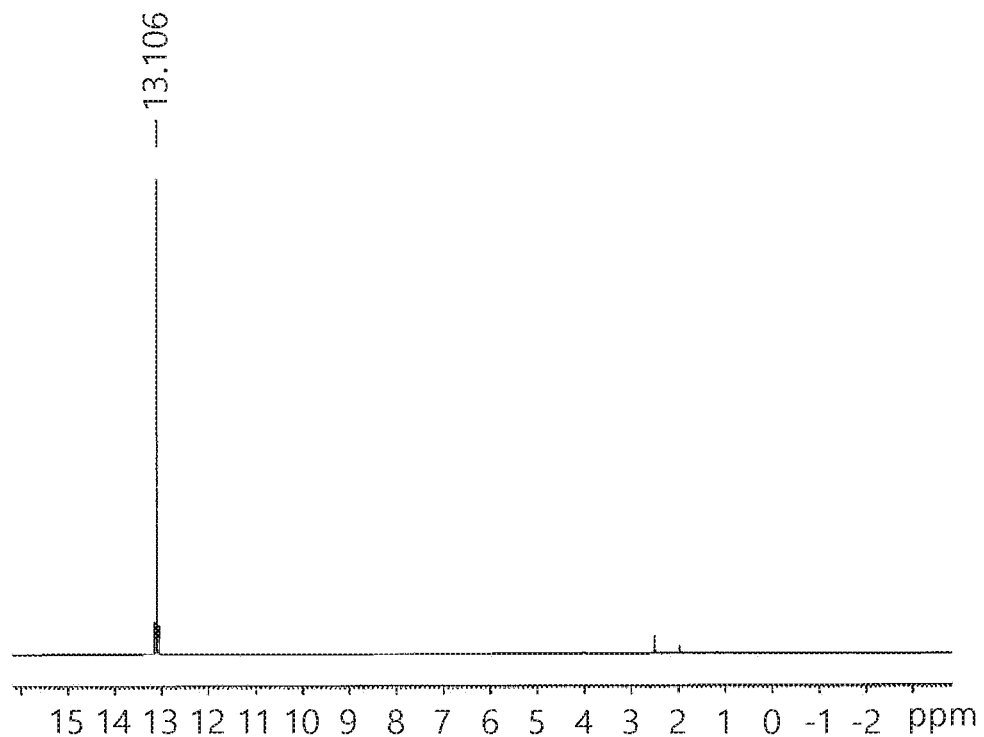
FIG. 4 illustrates NMR graphs of DCG synthesized in Example 2 of the present invention.
Figure 4B:
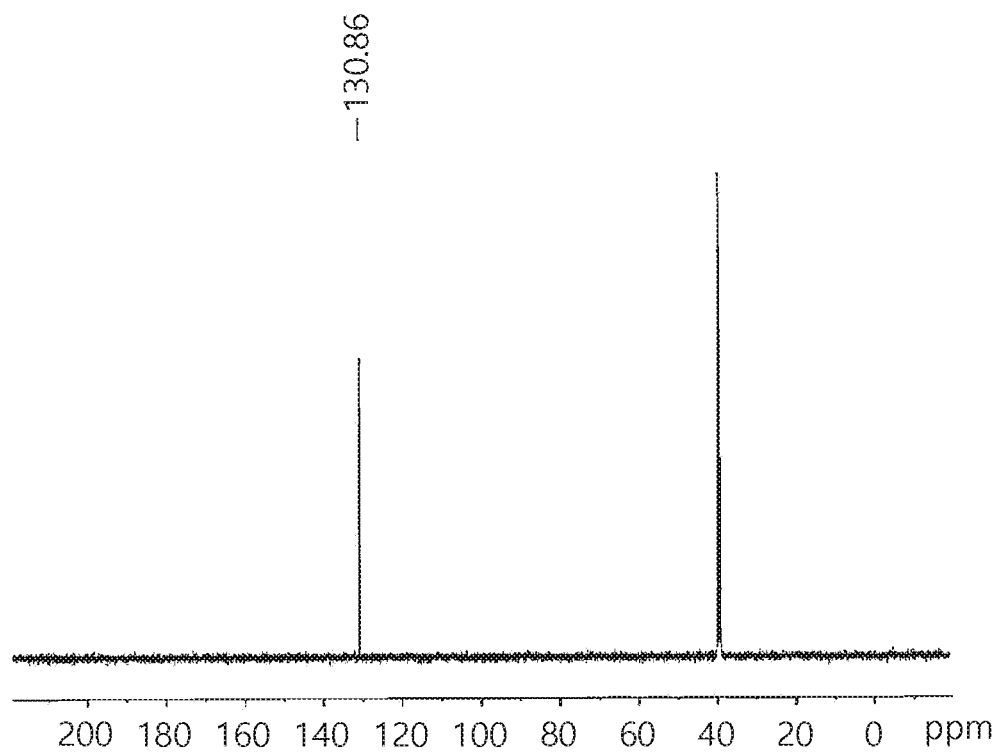

FIG. 4 illustrates NMR graphs of the DCG synthesized in Example 2 of the present invention. More specifically, FIG. 4A is a $^1$H NMR spectrum of the DCG and FIG. 4B is a $^{13}$C NMR spectrum of the DCG.

Referring to FIGS. 4A and 4B, it may be found that the DCG was synthesized based on Example 2.

Figure 5A:
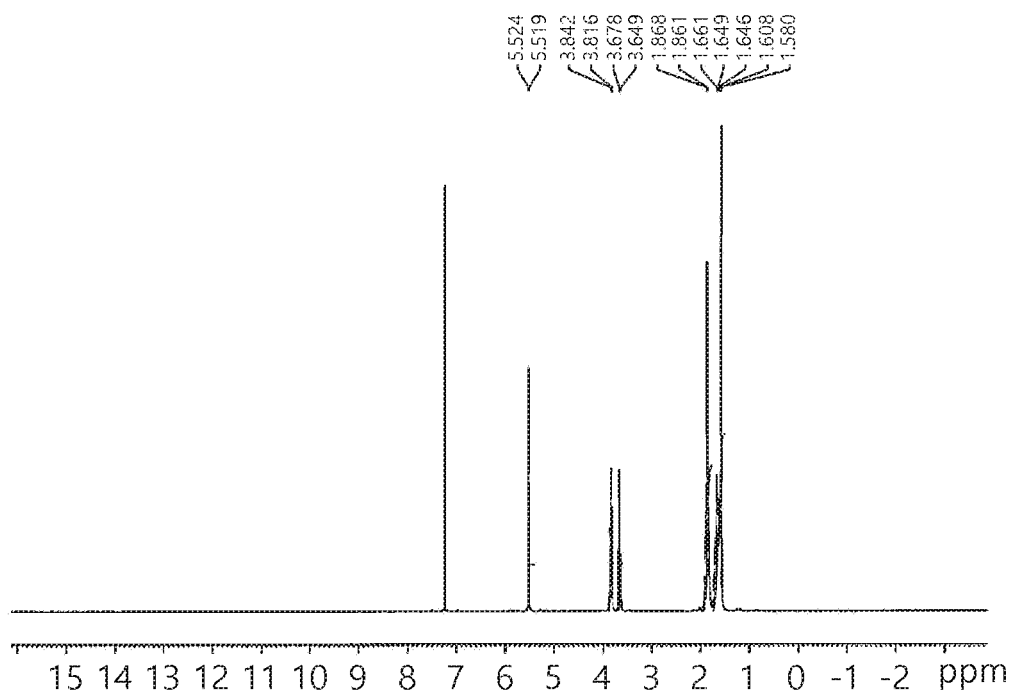
FIG. 5 illustrates NMR graphs of THP-DCG synthesized in Example 3 of the present invention.
Figure 5B:
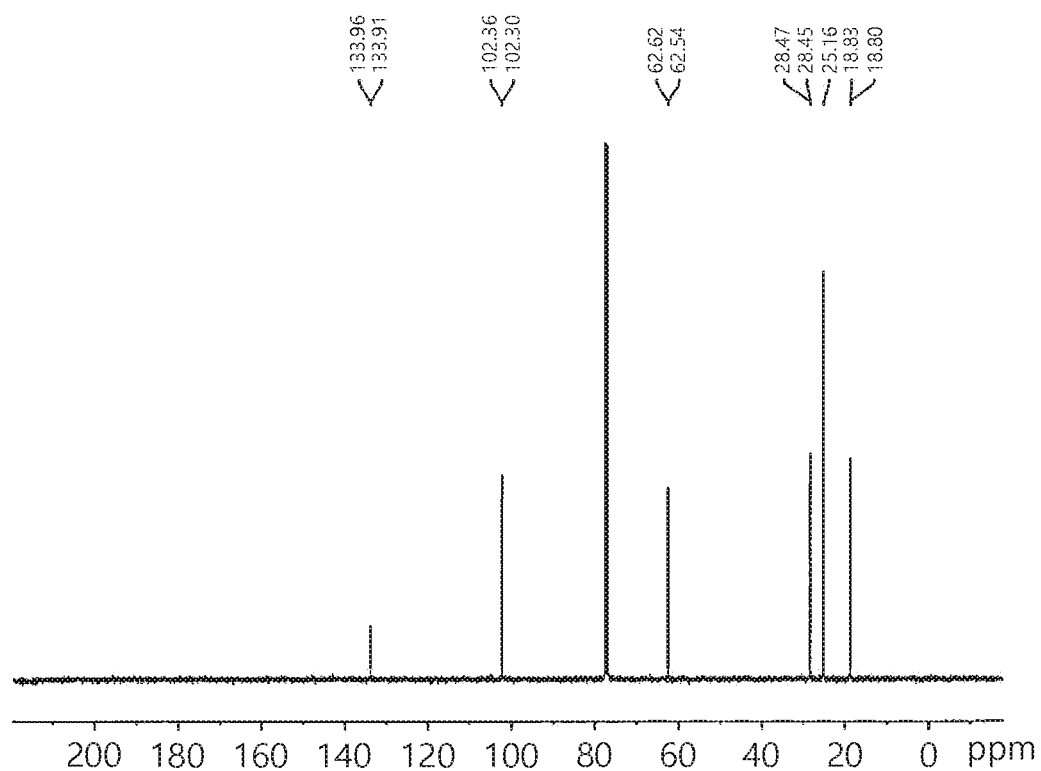

FIG. 5 illustrates NMR graphs of the THP-DCG synthesized in Example 3 of the present invention. More specifically, FIG. 5A is a $^1$H NMR spectrum of the THP-DCG and FIG. 5B is a $^{13}$C NMR spectrum of the THP-DCG.

Referring to FIGS. 5A and 5B, it may be found that the THP-DCG was synthesized based on Example 3.

Figure 6A:
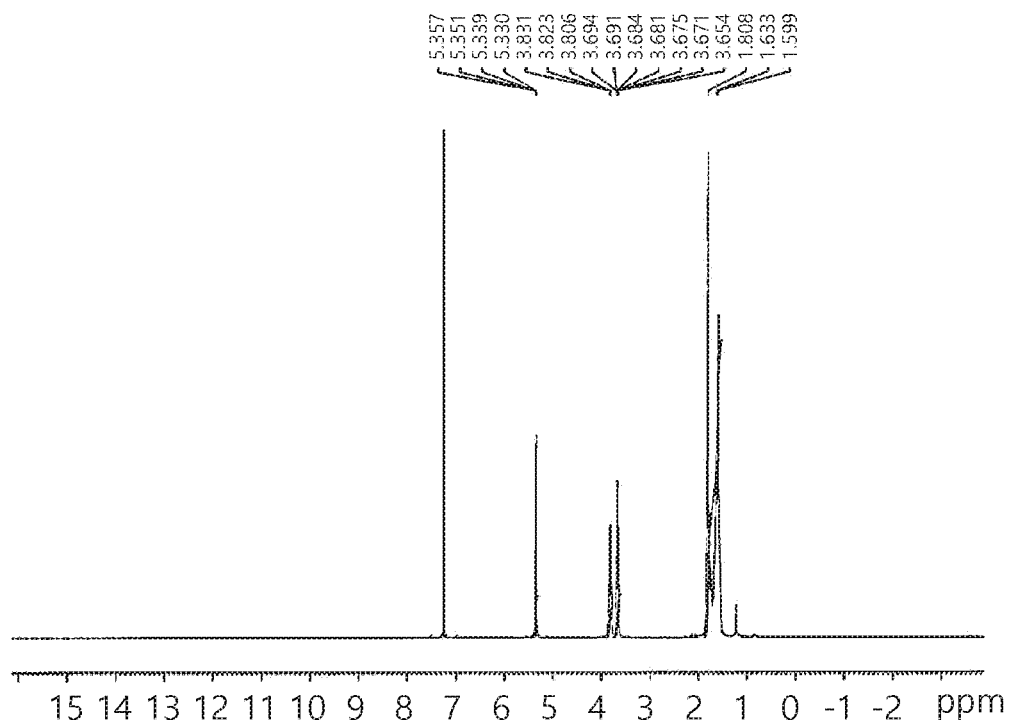
FIG. 6 illustrates NMR graphs of THP-DAG synthesized in Example 4 of the present invention.
Figure 6B:
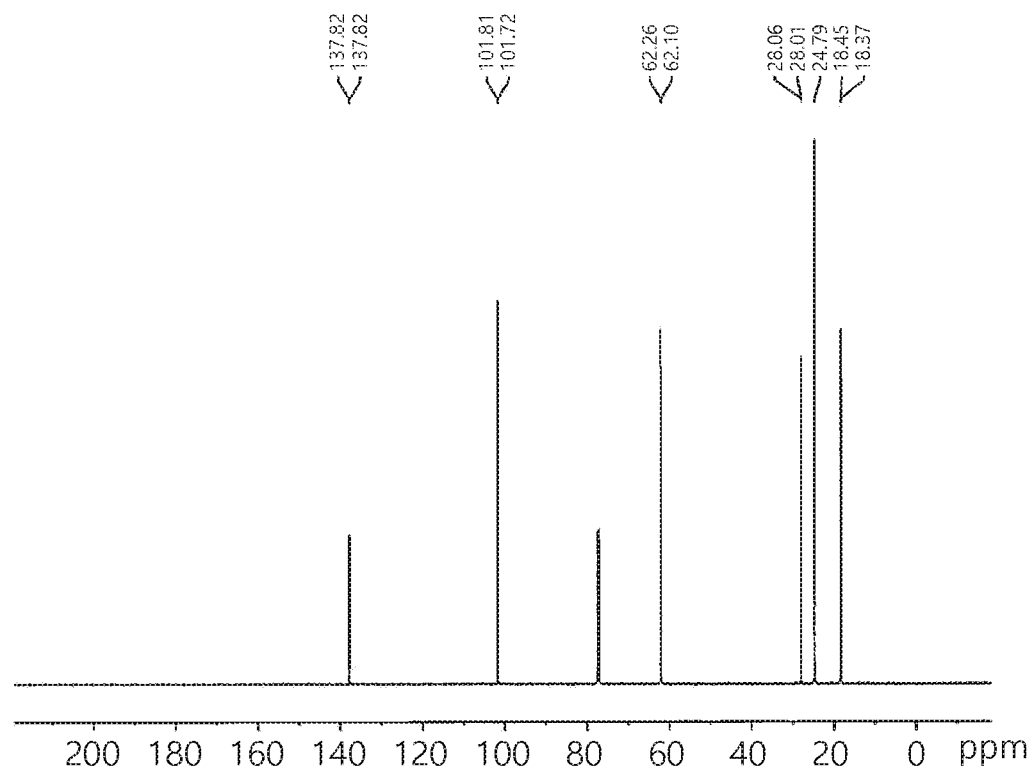

FIG. 6 illustrates NMR graphs of the THP-DAG synthesized in Example 4 of the present invention. More specifically, FIG. 6A is a $^1$H NMR spectrum of the THP-DAG and FIG. 6B is a $^{13}$C NMR spectrum of the THP-DAG.

Referring to FIGS. 6A and 6B, it may be found that the THP-DAG was synthesized based on Example 4.

Figure 7A:
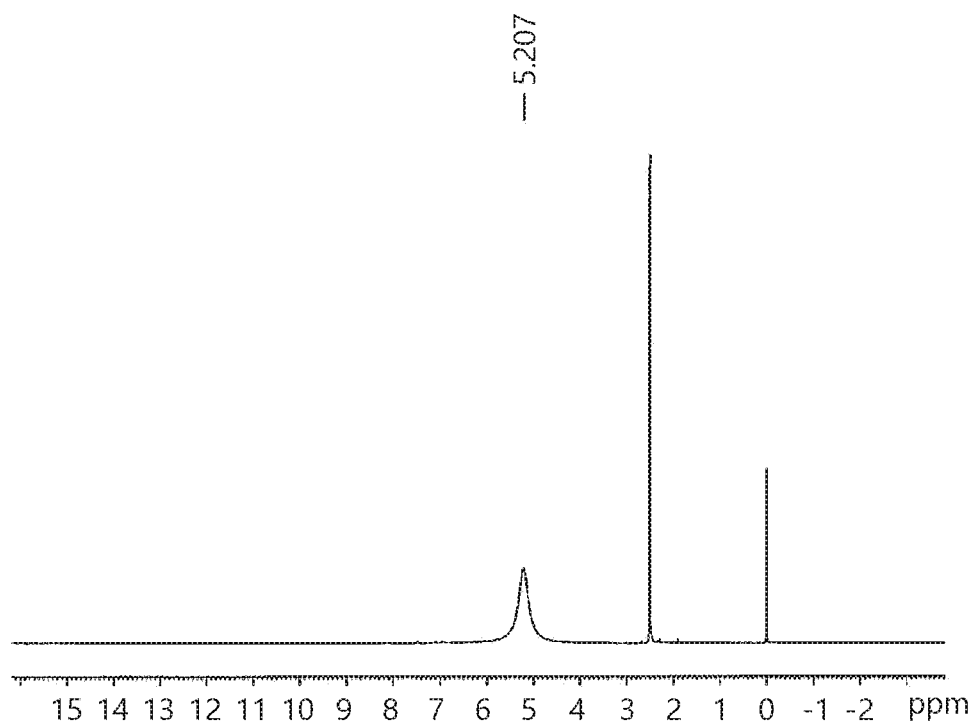
FIG. 7 illustrates NMR graphs of 1,1'-BTO synthesized in Example 5 of the present invention.
Figure 7B:
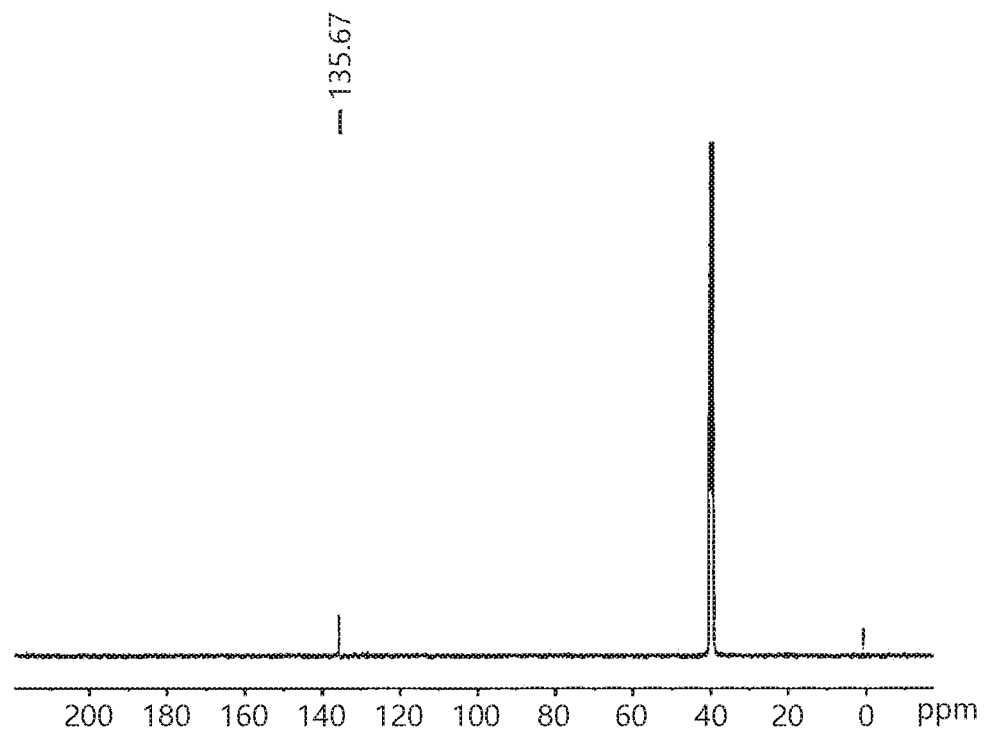

FIG. 7 illustrates NMR graphs of the 1,1'-BTO synthesized in Example 5 of the present invention. More specifically, FIG. 7A is a $^1$H NMR spectrum of the 1,1'-BTO and FIG. 7B is a $^{13}$C NMR spectrum of the 1,1'-BTO.

Referring to FIGS. 7A and 7B, it may be found that the 1,1'-BTO was synthesized based on Example 5.

Figure 8A:
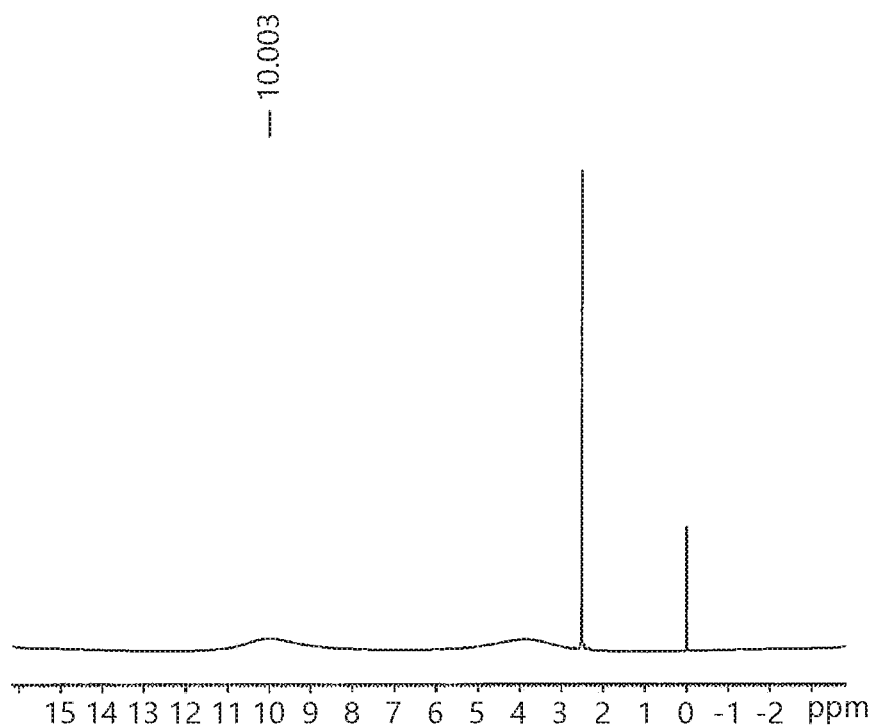
FIG. 8 illustrates NMR graphs of TKX-50 synthesized in Example 6 of the present invention.
Figure 8B:
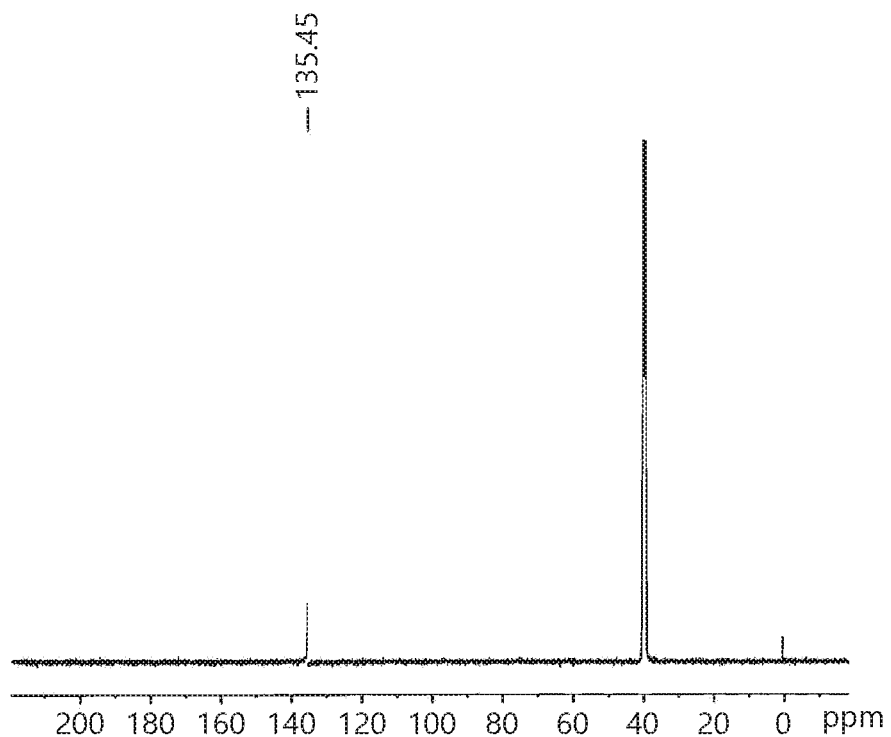

FIG. 8 illustrates NMR graphs of the TKX-50 synthesized in Example 6 of the present invention. More specifically, FIG. 8A is a $^1$H NMR spectrum of the TKX-50 and FIG. 8B is a $^{13}$C NMR spectrum of the TKX-50.

Referring to FIGS. 8A and 8B, it may be found that the TKX-50 was synthesized to based on Example 6.

As described above, the present invention relates to a method for synthesizing TKX-50 through THP-DAG that is an intermediate with an enhanced insensitivity, instead of DAG that is a sensitive intermediate and that is synthesized during synthesis of TKX-50, and is advantageous in that work is safely performed from threats of explosion and fire accidents caused by shock, friction and static electricity, in comparison to existing synthesis methods.

While the example embodiments have been shown and described with reference to the accompanying drawings, it will be apparent to those skilled in the art that various modifications and variations can be made from the foregoing descriptions. For example, adequate effects may be achieved even if the foregoing processes and methods are carried out in different order than described above, and/or the aforementioned elements are combined or coupled in different forms and modes than as described above or be substituted or switched with other components or equivalents. Thus, other implementations, alternative embodiments and equivalents to the claimed subject matter are construed as being within the appended claims.

The invention claimed is:

1. A method of manufacturing

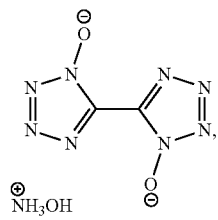

(TKX-50)

the method comprising:

preparing

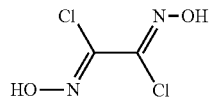

(DCG)

as a starting material;
forming a

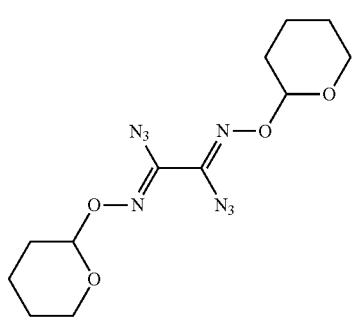
(THP-DAG intermediate)

from the DCG; and
synthesizing TKX-50 through the THP-DAG intermediate.

2. The method of claim 1, wherein the TKX-50 is free of

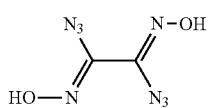
(DAG)

that is an intermediate byproduct.

3. The method of claim 1, wherein the method comprises:
synthesizing DCG;
synthesizing

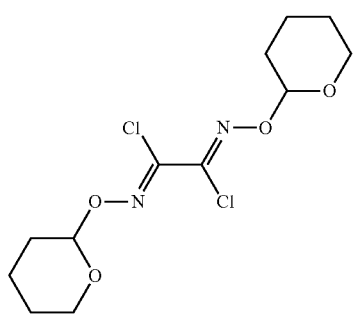
(THP-DCG)

through the DCG;
synthesizing THP-DAG through the THP-DCG; and
synthesizing TKX-50 through the THP-DAG.

4. The method of claim 3, wherein the synthesizing of the DCG comprises:
synthesizing glyoxime; and
reacting the glyoxime with N-chlorosuccinimide.

5. The method of claim 3, wherein the synthesizing of the THP-DCG through the DCG is performed by reacting the DCG with 3,4-dihydro-2H-pyran in the presence of a p-toluenesulfonic acid (p-TsOH) catalyst.

6. The method of claim 5, wherein the synthesizing of the THP-DCG through the DCG is performed by stirring and reacting the DCG, the p-TsOH and the 3,4-dihydro-2H-pyran at a weight ratio of 1:3 to 4:1.6.

7. The method of claim 6, wherein stirring of the DCG, the p-TsOH and the 3,4-dihydro-2H-pyran is performed at room temperature.

8. The method of claim 3, wherein the synthesizing of the THP-DAG through the THP-DCG is performed through an azidation reaction.

9. The method of claim 8, wherein the synthesizing of the THP-DAG through the THP-DCG is performed by reacting the THP-DCG with sodium azide (NaN$_3$).

10. The method of claim 9, wherein the THP-DCG and the sodium azide are stirred at a weight ratio of 1:0.4 to 0.8 and reacted.

11. The method of claim 10, wherein stirring of the THP-DCG and the sodium azide is performed at a temperature of 95° C. to 100° C.

12. The method of claim 3, wherein the synthesizing of the TKX-50 through the THP-DAG comprises:
synthesizing 5,5'-bistetrazole-1,1'-diol by reacting the THP-DAG with a hydrochloric acid gas; and
synthesizing the TKX-50 by reacting the 5,5'-bistetrazole-1,1'-diol with hydroxylamine.

13. The method of claim 12, wherein the synthesizing of the 5,5'-bistetrazole-1,1'-diol by reacting the THP-DAG with the hydrochloric acid gas is performed by stirring the THP-DAG and the hydrochloric acid under a temperature condition of room temperature.

14. The method of claim 12, wherein the synthesizing of the TKX-50 by reacting the 5,5'-bistetrazole-1,1'-diol with the hydroxylamine is performed by stirring and reacting the 5,5'-bistetrazole-1,1'-diol and the hydroxylamine at a weight ratio of 1:0.5 to 0.7.

15. The method of claim 14, wherein stirring of the 5,5'-bistetrazole-1,1'-diol and the hydroxylamine is performed at a temperature of 40° C. to 60° C.

* * * * *